(12) United States Patent
Yun et al.

(10) Patent No.: US 8,318,191 B2
(45) Date of Patent: *Nov. 27, 2012

(54) POROUS MATERIAL HAVING HIERARCHICAL POROUS STRUCTURE AND PREPARATION METHOD THEREOF

(75) Inventors: Huisuk Yun, Changwon-Si (KR); Seung-Eon Kim, Changwon-Si (KR); Yongtaek Hyung, Changwon-Si (KR)

(73) Assignee: Korean Institute of Machinery & Materials, Daejeon (KR)

( * ) Notice: Subject to any disclaimer, the term of this patent is extended or adjusted under 35 U.S.C. 154(b) by 937 days.

This patent is subject to a terminal disclaimer.

(21) Appl. No.: 12/253,054

(22) Filed: Oct. 16, 2008

(65) Prior Publication Data
US 2010/0010513 A1 Jan. 14, 2010

(30) Foreign Application Priority Data
Jul. 14, 2008 (KR) .................. 10-2008-0068146

(51) Int. Cl.
 A61F 2/00 (2006.01)
 A61B 17/08 (2006.01)
 C01B 25/10 (2006.01)

(52) U.S. Cl. ......... 424/423; 424/424; 606/151; 423/301

(58) Field of Classification Search .............. 424/423, 424/424; 606/151; 423/301
See application file for complete search history.

(56) References Cited

U.S. PATENT DOCUMENTS

| 7,799,839 | B2 * | 9/2010 | Yun et al. .................. 521/61 |
| 2006/0246121 | A1 | 11/2006 | Ma et al. |
| 2008/0103227 | A1 * | 5/2008 | Yun et al. .................. 523/105 |
| 2009/0252795 | A1 * | 10/2009 | Smyth ........................ 424/484 |

FOREIGN PATENT DOCUMENTS

| JP | 2005-22929 | 1/2005 |
| JP | 2006-290680 | 10/2006 |
| JP | 2007-046042 | 2/2007 |
| KR | 2006-103013 | 10/2006 |
| KR | 751504 | 8/2007 |
| WO | 0149606 | 7/2001 |

OTHER PUBLICATIONS

Subhash Baral, Paul Schoent; Chem. Mater. 1993.5.145.
C.T. Kresge, et al.; Nature 1992, 359, 710.
Christine G. Goeltner, et al.; Angew. Chem. Int. Ed. 1998, 37, 613.
(Continued)

*Primary Examiner* — Aradhana Sasan
(74) *Attorney, Agent, or Firm* — Lucas & Mercanti, LLP

(57) ABSTRACT

Disclosed are porous ceramic balls with a hierarchical porous structure ranging in size from nanometers to micrometers, and preparation methods thereof. Self-assembly polymers and sol-gel reactions are used to prepare porous ceramic balls in which pores ranging in size from ones of nanometers to tens of micrometers are hierarchically interconnected to one another. This hierarchical porous structure ensures high specific surface areas and porosities for the porous ceramic balls. Further, the size and distribution of the pores can be simply controlled with hydrophobic solvent and reaction time. The pore formation through polymer self-assembly and sol-gel reactions can be applied to ceramic and transition metals. Porous structures based on bioceramic materials, such as bioactive glass, allow the formation of apatite therein and thus can be used as biomaterials of bioengineering, including bone fillers, bone reconstruction materials, bone scaffolds, etc.

20 Claims, 13 Drawing Sheets

(a)

(b)

OTHER PUBLICATIONS

Markus Antonietti, et al.; Adv. Mater. 1998, 10, 154.
Limin Qi, et al.; J. Phys. Chem. B. 1997, 101, 3460.
S. Schacht, et al.; Science, 1996, 273, 768.
Cheng Tao, et al.; Colloids and Surf. A. 2005, 256, 57.
A. Imhof et al.; Nature, 1997, 389, 948.
Dongyuan Zhao, et al.; J. Am. Chem. Soc. 1998, 120, 6024.
Katsunori Kosuge, et al.; Chem Mater. 2004, 16, 4181.
Abstract of conference of the Korean ceramic society, Apr. 24, 2008.
Program of the International Symposium on New Frontier of Advanced Si-Based Ceramics and Composites, Jun. 8-11, 2008.

* cited by examiner

POROUS MATERIAL HAVING HIERARCHICAL POROUS STRUCTURE AND PREPARATION METHOD THEREOF

CROSS-REFERENCE TO RELATED APPLICATIONS

This application claims the benefit of Korean Patent Application No. 10-2008-0068146 filed Jul. 14, 2008, the contents of which are incorporated herein by reference.

BACKGROUND OF THE INVENTION

1. Field of the Invention

The present invention relates to porous ceramic balls with a hierarchical porous structure, and a method for preparing the same.

2. Description of the Related Art

Porous materials finds a broad spectrum of applications in many fields, including catalysts and catalyst support, filters, separation/permeable membranes, electrodes, absorbents, scaffold, etc. The control of morphology and porosity thereof plays an important role in improving the properties of porous materials. With an ability to effect a great improvement in surface area, porosity, permeability and selectivity, particularly, porous materials in which hierarchical porous structures such as secondary or tertiary porous structures are formed, are expected to be applicable to various newly arising fields of application including drug delivery systems, biosensors, permeable membranes, filters, etc. Many methods have recently been suggested for the synthesis of porous materials which have a hierarchical porous structure.

For the synthesis of three-dimensional porous structures, many methods are known, including a particle leaching method, a gas foaming method, a fiber mesh method, a phase separation method, an emulsion freeze drying method, etc. However, these synthesis methods find it difficult to control pore sizes and are apt to produce structures which are relatively low in surface area and porosity. In addition, the porous materials obtained by conventional methods hold poor interporous open structures, suffering from pore plugging. Recently, rapid prototyping, which is the automatic construction of physical objects with the aid of a computer system, has been suggested for the construction of supports. This technique arises as a solution to the problems of conventional methods and is effective for constructing three-dimensional porous structures which have pore sizes (giant pores: 100-1000 μm) of sufficient size to support the growth of cells.

Conventionally, pore sizes of porous materials are, for the most part, controlled over giant size ranges. In expectation of improvements in cell adhesion, cell proliferation, cell differentiation and prevention of cell necrosis as well as an increase in specific surface area and porosity, control has recently been concentrated on directing the size and morphology of pores, such as double pores (Korean Patent No. 751504) or triple pores (Korean Patent Application No. 2006-103013) within nano, macro, and giant pore ranges. Particularly, studies on the introduction of nano-pores into supports have been conducted in expectation of increasing bioactivity and biodegradability and helping delivery of anticancer and anti-inflammatory agents. Korean Patent Publication No. 2006-105013 describes the synthesis of ceramic supports with giant-, macro-, nano-size pores or ceramic-polymer supports with giant- or nano-size pores using a rapid prototyping or polymer template method, and adds to the significance of structures having multiple pores.

However, the conventional porous ceramic structures show mechanical properties insufficient for use in supports. Although improved in physical strength, the ceramic-polymer supports contain giant- and nano-size pores, but lack macro-size pores which can be used as migration paths for active materials, such as cell nutrients and discharge from cells.

Also, the use of endogenous plates is applied for the construction of self-assembly polymer structures (S. Baral et al., Chem. Mater. 1993. 5. 145), lyotropic liquid crystal structures (C. T. Kresge et al., Nature 1992, 359, 710), mesoporous structures of block copolymers (M. Antonietti et al., Angew. Chem. Int. Ed. 1998. 37. 613), and colloidal arrays (H. P. Nentze et al., Adv. Mater. 1998. 10.154). In addition, construction methods taking advantage of complex morphology based on the topological defects and interfacial defects of inorganic-organic structures (Z. Zhao et al, J. Phys. Chem. B. 1997. 101. 3460) and oil-in-water droplets (F. Schuth et al., Science. 1996. 273. 768), water-in-oil (J. Li et al., Colloids and Surf. A. 2005. 256. 57), and emulsion bubbles (D. J. Pine et al., Nature. 1997. 389. 948) have been suggested.

The G. D. Stucky and M. Takemori group reported a block copolymer template method by which nano- and meso-porous structures with pores ranging from 2 to 50 nm can be constructed (J. Am. Chem. Soc. 1998. 120. 6024; Chem. Mater. 2004. 16. 4181)).

The conventional methods described above are problematic because multi-step processes are required for the methods, and a combination of two or more templates is required for the construction of porous structures having nano-size pores which are limited to two or fewer types.

Leading to the present invention, the application of polymer self-assembly and sol-gel reaction to the formation of porous ceramic balls resulted in the finding that the porous ceramic balls have three-dimensional hierarchical porous structures therein and a large specific surface area and a large porosity, with pores interconnected therebetween, and can be used as bone scaffolds.

SUMMARY OF THE INVENTION

Accordingly, the present invention has been made keeping in mind the above problems occurring in the prior art, and an object of the present invention is to provide porous ceramic balls with a hierarchical porous structure.

Another object of the present invention is to provide a method for preparing the porous ceramic balls having a hierarchical porous structure.

In order to accomplish one object of the present invention, the present invention provides porous ceramic balls, having a hierarchical porous structure in which pores with a size of 10~100 μm are constructed, with pores having a size of 0.1~10 μm formed on the surface thereof, and pores with a size of 1~100 nm formed on the surface of the pores having a size of 0.1~10 μm, said pores being interconnected with one another.

Also, the other object of the present invention may be accomplished by a provision of a method for preparing a porous ceramic ball, comprising: preparing a polymer template solution (step 1); preparing a precursor solution (step 2); mixing and reacting the polymer template of step 1 with the precursor of step 2 to give a mixed solution having an increased viscosity (step 3); immersing the mixed solution of step 3 in a hydrophobic solvent to form reverse micelles and subjecting the reverse micelles to a sol-gel reaction to produce a ball (step 4); and aging, drying, and thermally treating the ball of step 4 to remove the polymer template therefrom (step 5).

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

In accordance with an aspect thereof, the present invention pertains to porous ceramic balls with hierarchical pore structures ranging in size from nanometers to micrometers.

In the hierarchical porous structures, pores ranging in size from 0.1 to 10 µm are formed on the walls of pores 10-100 µm in size and contain 1-100 nm pores on the walls thereof, with interconnections therebetween. Depending on sizes, the hierarchical porous structure can be applied to selective adsorption and separation. Also, providing large porosity and large specific surface areas, they can be used as catalyst support, filters, construction materials, biomaterials, etc.

The porous ceramic balls can be prepared in sizes of 100-3000 µm under the control of solution viscosity, syringe needle size, the distance between the syringe and the non-polar solvent, and properties of the non-polar solvent.

Preferably, the porous ceramic balls range in size from 100 to 3000 µm. The porous ceramic balls are difficult to prepare in a size less than 100 µm. Porous ceramic balls larger than 3000 µm show low mechanical strength.

As for the ceramic, it may be selected from among silica, dioxide, titania, zirconia, alumina, calcium oxide, phosphorus oxide, and combinations thereof. However, as long as it can be prepared into porous balls through a sol-gel reaction, any ceramic may be used in the present invention.

When the porous ceramic balls are used as catalyst support, filters, construction materials or biomaterials, the porosity and specific surface area thereof are factors determining the functions of the balls. It is preferred that the porosity and the specific surface area be between 40% and 80% and between 100 $m^2/g$ and 1000 $m^2/g$, respectively.

The porosity and the specific surface area outside the respective ranges cause the balls to decrease in absorptive and discharge efficiency, giving rise to lowering the functionality of products using the balls.

In accordance with another aspect thereof, the present invention pertains to a method for preparing porous ceramic balls, comprising: preparing a self-assembly polymer template solution (step 1); preparing a precursor solution (step 2); mixing and reacting the polymer template solution of step 1 with the precursor solution of step 2 to increase viscosity (step 3); adding dropwise the mixture of step 3 into a hydrophobic solvent to form reverse micelles and subjecting the reverse micelles to a sol-gel reaction to form balls (step 4); and aging and drying the balls of step 4, followed by thermal treatment to remove the polymer template (step 5).

Figure 1:
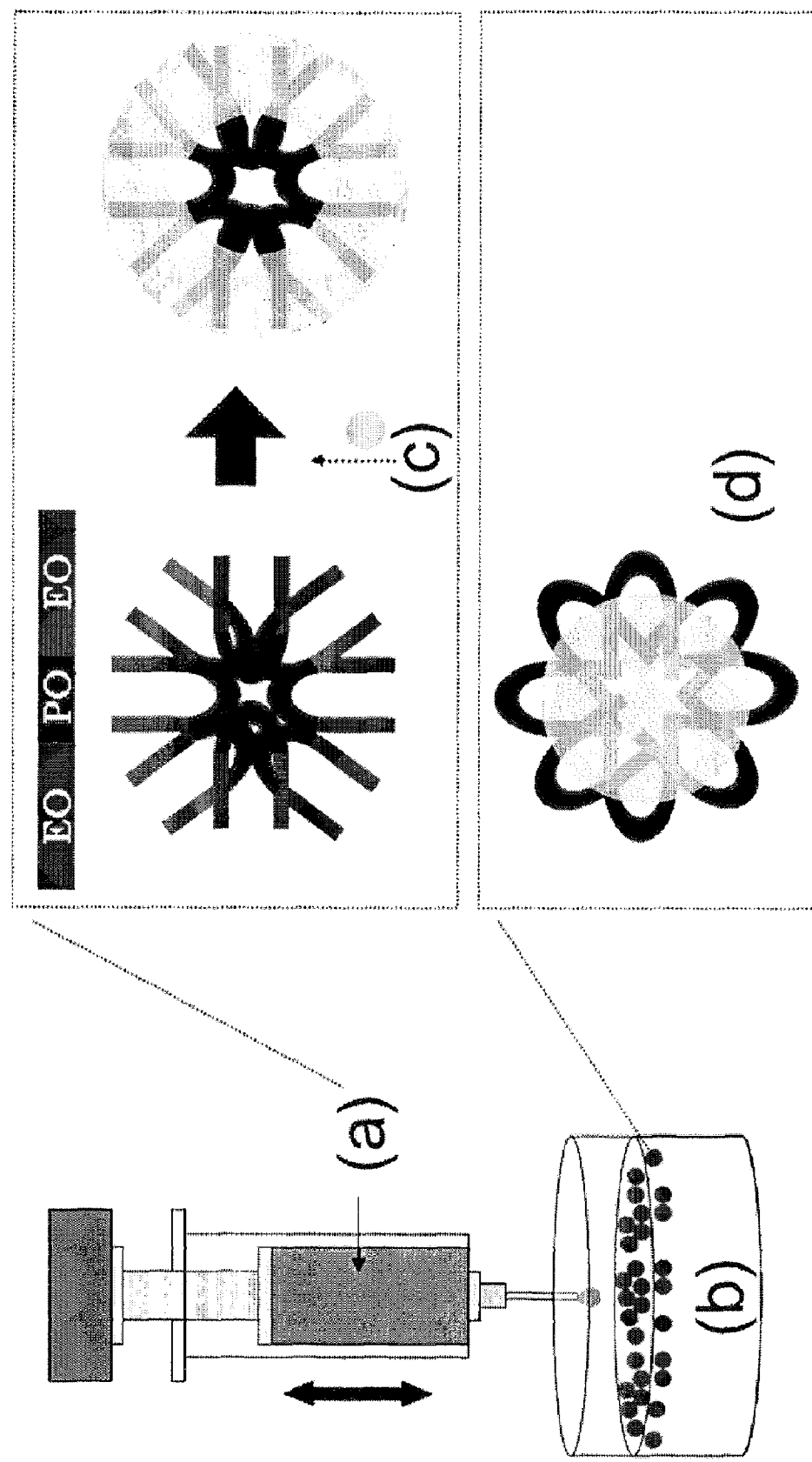
FIG. 1 is a schematic view showing a preparation method of porous ceramic balls in accordance with the present invention (organic-inorganic self-assembly solution (a), hydrophobic solvent (b), addition of inorganic precursors (c), formation of reverse micelles (d))
Figure 8:
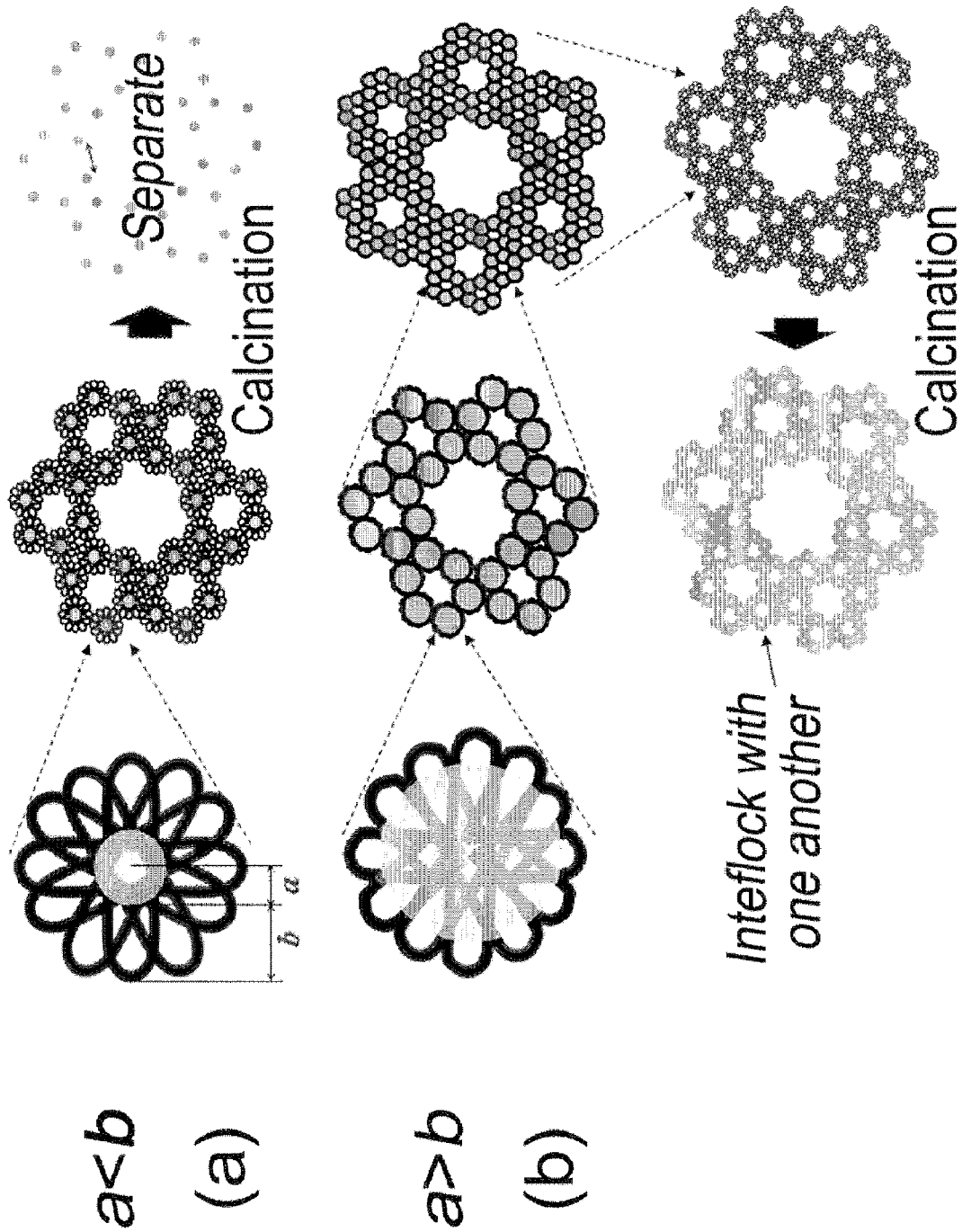
FIG. 8 is a diagram illustrating the mechanism of forming porous ceramic balls according to an embodiment of the present invention.

Together with their preparation procedure, the principle of forming the porous ceramic balls having hierarchical porous structures in accordance with the present invention is illustrated in FIGS. 1 and 8.

As shown in FIG. 1, a tri-block copolymer which can be used as a template due to the self-assembly property thereof directs the hydrophilic moieties thereof towards the outside in a hydrophilic environment, forming self-assembly micelles. Then, these self-assembly micelles are allowed to associate with a hydrophilic inorganic precursor to afford inorganic-organic nano-self-assembly structures. When added dropwise to a hydrophobic solvent, the inorganic-organic nano-self-assembly structures experience rearrangement in such a way that the internal hydrophobic moieties of the micelles direct towards the outside with both the hydrophilic moieties and the inorganic precursor located inside, resulting in the formation of reverse micelles.

During a sol-gel reaction, the inorganic precursors of the reverse micelles tend to aggregate together. As schematically illustrated in FIG. 8, however, when the hydrophobic moiety of the polymer template is long (a), it inhibits the aggregation of inorganic precursors present within adjacent reverse micelles so that the inorganic precursors form nano-particles only. On the other hand, when the hydrophobic moiety is short (b), adjacent reverse micelles aggregate to micelles in nano-sizes which in turn aggregate to micelles in micrometers. Removal of the polymer template leaves porous ceramic balls with hierarchical porous structures.

Below, the formation of the hierarchical porous structures is described in a stepwise manner.

Step 1 of the preparation method of porous ceramic balls in accordance with the present invention is the preparation of a polymer template solution.

In this step, a template polymer is dissolved in a water-soluble polar solvent to form self-assembly micelles in which the hydrophilic moieties of the polymer are exposed to the outside with the hydrophobic moiety directed internally.

For use in the formation of the micelles, the polymer is preferably a tri-block polymer composed of (hydrophilic moiety)$_x$(hydrophobic moiety)$_y$(hydrophilic moiety)$_x$.

The hydrophilic moiety may be selected from a group consisting of poly alkyl(acrylic) acid, polyacrylamide, poly (N,N-dimethyl acrylamide), poly(N-isopropyl acrylamide), poly(ethylene glycol), poly(ethylene oxide), poly(methyl vinyl ether)), poly(styrene sulfonic acid), poly(vinyl alcohol), poly(2-vinyl N-methylpyridinium iodide), poly(N-vinyl imidazole) poly(ethylene imine), and combinations thereof.

Examples of the polyalkyl(acrylic)acid include poly (acrylic acid), poly($\alpha$-ethylacrylic acid), poly($\alpha$-propylacrylic acid), poly(methacrylic acid), poly(sodium acrylate), poly(sodium methacrylate) and poly(2-hydroxyethyl methacrylate). As for the poly(ethylene imine), poly(N-vinylamine), poly(N-vinyl formamide), poly(N-vinyl isobutyramide) or poly(N-vinyl pyrrolidone) may be employed therefor.

Concrete examples of the hydrophobic moiety useful in the tri-block polymer of the present invention include polyolefins, poly alkyl(acrylate), polybutadiene, polyisoprene, poly (N-vinyl imidazole), polylactone (lactide), polyisobutyl, polyoxirane, polyvinylpyridine, polysiloxane, polystyrene, poly(acrylonitrile), poly(adipic anhydride), poly(ethylene terephthalate), poly(ferrocenyldimethylsilane), poly(N-vinyl caprolactam), poly(N-vinyl carbazole), poly(sulfone ether), poly(vinyl acetate), polycarbonate, polyconidine, poly vinyl napthalene and poly vinyl anthracene.

The polyolefins useful in the present invention have a backbone chain of 1-20 carbons. Within the range of the polyalkyl acrylate useful in the present invention may fall the following: poly(benzyl $\alpha$-ethyl acrylate)), poly(benzyl $\alpha$-propyl acrylate)), poly(cyclohexyl methacrylate), poly(ethyl acrylate), poly(isopropyl acrylate), poly(ethyl methacrylate), poly (ethyl $\alpha$-ethyl acrylate), poly(ethyl $\alpha$-propyl acrylate), poly (fluorescein O-methacrylate), poly(glycidyl methacrylate), poly(hydroxy propyl acrylate), poly(isobornyl methacrylate), poly(iso-butyl methacrylate), poly(isocyanato ethyl methacrylate), poly(lauryl methacrylate), poly(methyl acrylate), poly(methyl $\alpha$-bromoacrylate), poly(methyl methacrylate)-atactic), poly(N,N-dimethylaminoethyl methacrylate)), poly(n-butyl acrylate), poly(n-butyl methacrylate), poly(neopentyl methacrylate), poly(n-hexyl methacrylate), poly(n-nonyl acrylate), poly(n-nonyl methacrylate), poly(n-octyl acrylate), poly(n-propyl methacrylate), poly(octadecyl methacrylate), poly(s-butyl methacrylate), poly(t-butyl acrylate), poly(t-butyl methacrylate), Poly(t-butyl $\alpha$-bromo-acrylate), poly(t-butyl $\alpha$-ethylacrylate), poly(t-butyl $\alpha$-propylacrylate), poly(tetrahydrofurfanyl methacrylate), poly(2,4-dimethyl-2, 4-pentadienoate), poly(2-ethyl hexyl acrylate), poly(2-ethyl hexyl methacrylate), poly(2-hydroxypropyl methacrylate) and poly(9-Anthracenyl methyl methacrylate).

As for the polyoxirane, it may be exemplified by poly (propylene oxide), poly(propylene glycol) dimethyl ether) and poly(2,6-dimethyl-p-phenylene oxide) Examples of the polysioxane include poly(dimethyl siloxane), poly(ethyl methyl siloxane), poly(phenyl methyl siloxane) and poly(diethyl siloxane). For the polystyrene, selection may be conducted among poly($\alpha$-methyl styrene), poly(4-acetoxy styrene), polybromostyrene, polychlorostyrene, poly(4-dimethylsilyl styrene), poly(4-hydroxyl styrene)), poly(4-methoxy styrene), poly(4-methyl styrene), poly(4-t-butyl styrene), poly(vinyl benzyl chloride) and poly(vinyl benzoic acid).

In the tri-block polymer composed of (hydrophilic moiety)$_x$(hydrophobic moiety)$_y$(hydrophilic moiety)$_x$, the ratio x:y preferably ranges from 0.5:1 to 1000:1. More preferably, the ratio x:y is between 0.7:1 and 500:1. If the ratio of x to y is below 0.5, the hydrophilic moieties are long enough to lower attraction between the precursors, so that adjacent ceramic precursors cannot be interconnected therebetween, resulting in the formation of nanoparticles of nano-sizes. On the other hand, even when the ratio of x to y exceeds 1000 yet is set to have an upper limit, the tri-block polymer may be used without limitations.

Step 2 of the preparation method of porous ceramic balls in accordance with the present invention is preparation of a precursor solution.

The precursor solution is ionized through a sol-gel reaction to serve as an inorganic source for the ceramic balls. As long as it forms sol-gel, any precursor solution may be used in the present invention.

Step 3 of the preparation method of porous ceramic balls in accordance with the present invention is mixing and reacting the polymer template solution of step 1 with the precursor solution of step 2 to increase viscosity.

In step 3, the polymer micelles with hydrophilic moieties in contact with surrounding polar solvent, with the hydrophobic moieties sequestered in the micelle center, are slowly subjected to polycondensation with the inorganic source polymer in the sol-gel solution of step 2 to afford a solution of organic-inorganic polymer self-assembly micelles which is viscous enough to maintain the morphology of ceramic balls when they are added thereto.

The viscosity can be adjusted by drying the solvent preferably into a range of 2000-35000 cps. When the viscosity is below 2000 cps, the ceramic balls cannot maintain a spherical shape. On the other hand, a viscosity exceeding 35000 cps allows sufficient polycondensation between hydrophilic moiety-reacted inorganic precursors, so that the reaction between inorganic particles exceeds the self-assembly ability of the polymer, causing the loss of a driving force for causing the rearrangement of the polymer template and thus failing to form pores in the ceramic balls.

Step 4 of the preparation method of porous ceramic balls in accordance with the present invention is the dropwise addition of the organic-inorganic self-assembly micelle solution of step 3 to a hydrophobic solvent to form ceramic balls.

In step 4, the organic-inorganic self-assembly micelle solution mixed in step 3 is added dropwise to a hydrophobic solvent to elicit self-assembly in which the hydrophobic moieties migrate to the surface in contact with the hydrophobic solvent with both the hydrophilic moieties and the inorganic precursors sequestered inside the micelles. At this time, the nano-structures of the precursor solution experiences rearrangement to give reverse-micelles.

The size and morphology of the balls depends on the viscosity of step 3, the internal diameter of the syringe needle, or the distance of dropping.

In addition, the hydrophobic solvent is preferably higher in viscosity than the ceramics, so that the balls do not sediment in the solvent and so maintain their spherical shape. Examples of the hydrophobic solvent useful in the present invention include chloroform, carbon tetrachloride, benzene, o-dichlorobenzene, toluene, xylene, pentane, mesitylene, cyclohexane, hexane, heptane diethylether, tetrachloroethylene acetonitrile, dimethylsulfoxide, dimethylformamide, trichloroethylene and mixtures thereof, with a preference for chloroform.

Step 5 of the preparation method of porous ceramic balls in accordance with the present invention is the ageing and drying of the balls of step 4, followed by the removal of the polymer template through thermal treatment.

In step 5, thermal treatment is conducted to remove the polymer template from the balls of step 4, thus leaving pores in the ceramic balls. In this regard, the thermal treatment is performed at 400-800° C. for 2-8 hours.

When the temperature for the thermal treatment is below 400° C., the polymer template is not completely removed and the remainder acts as impurities. On the other hand, a temperature higher than 800° C. destroys nano-pores, lowering the specific surface area. Further, when the thermal treatment is conducted for less than 2 hours, the polymer template is not completely removed, lowering the specific surface area. On the other hand, thermal treatment for longer than 8 hours destroys the nano pores, lowering the specific surface area.

In accordance with a further aspect thereof, the present invention provides bioactive bone scaffolds based on the porous ceramic balls.

As explained in Experimental Example 5, below, the porous ceramic balls with hierarchical porous structures in accordance with the present invention are superior in biocompatibility since the degradation of ceramic and the formation of apatite can occur sequentially or simultaneously in simulated body fluid. Thus, they can be used as such bone reconstructing materials as bone fillers and bone scaffolds. In addition, with chemical and physiological stability and porosity, the porous ceramic balls can be used as carriers in drug delivery systems for various drugs including anticancer agents, anti-inflammatory agents, hormonal agents, contraceptive agents, medications to help stop smoking, osteogenesis inducers and promoters.

Furthermore, the porous ceramic balls of the present invention are applicable to fields requiring high porosity and specific surface area, for example, the treatment of waste water which requires solid catalysts or catalyst support, the purification of discharge gas or the removal of VOC, and filters, separation membranes or ion exchange membranes for high-temperature, high-pressure water purification, $NO_x$ removal, and solid-liquid separation. Also, the porous ceramic balls are found in a wide range of applications in the construction field, including members for sound absorption or heat insulation.

A better understanding of the present invention may be obtained through the following examples which are set forth to illustrate, but are not to be construed as limiting the present invention.

EXAMPLE 1

Porous Ceramic Balls 1

Step 1. Preparation of Polymer Template Solution 3.46 g of the tri-block copolymer (Poly-ethylene oxide)$_{132}$ (Poly-propylene oxide)$_{50}$ (Poly-ethylene oxide)$_{132}$ was completely dissolved in 18.1 mL of ethanol at 40° C. for 0.5 to 1 hour with stirring, to afford a polymer template solution.

Step 2. Preparation of Precursor Solution 6 mL of tetraethyl orthosilicate was slowly mixed with 1.36 g of calcium nitrate tetrahydrate to homogeneity, followed by the addition of 0.26 mL of triethyl phosphate. Then, a mixture of 0.95 mL of 1 M HCl, 7.62 mL of ethanol and 2.86 mL of distilled water was added before stirring at 40° C. for 0.5-1 hour. Thus, a precursor solution resulted.

Step 3. Preparation of Mix Solution for Porous Ceramic Balls

To the solution of step 1 was added a B solution with slowly stirring. The resulting mixture was further stirred at 1000-1500 rpm for 2-4 hours and then incubated at −5 to 80° C. at RH 5~1000 for 24~48 hours in an incubator to induce a reaction between the inorganic source and the polymer template with the solvent slowly evaporating.

Step 4. Preparation of Ceramic Balls

After increasing in viscosity following evaporation of the solvent mixture in an incubator, the solution of step 3 was loaded into a syringe equipped with an extruder. Using the extruder, the viscous solution was dropped into chloroform, and incubated for from hours to days to form ceramic balls.

Step 5. Removal of Polymer Template

Following the removal of chloroform therefrom, the ceramic balls prepared in step 4 were aged and dried in an incubator. They were then thermally heated at an increment rate of 1° C./min for 4 hours to the final temperature of 400-800° C. in a calcinations furnace to remove the polymer from the porous ceramic balls.

Figure 3:
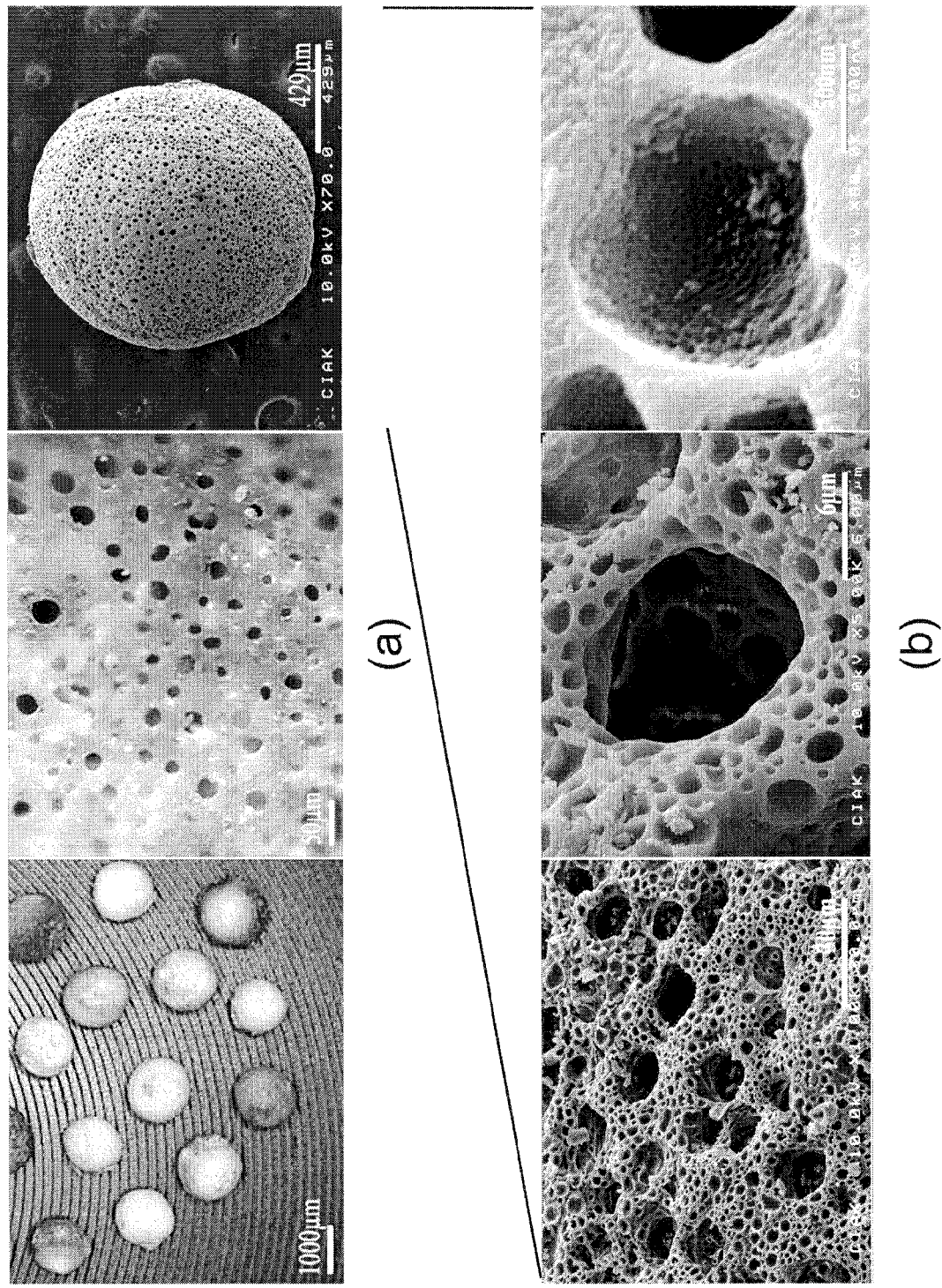
FIG. 3 is of scanning electron microphotographs of porous ceramic balls according to an embodiment of the present invention (low magnification (a), high magnification (b))

With reference to FIG. 3, the porous ceramic balls of Example 1 are shown in scanning electron microscope photographs.

As seen in FIG. 3, the porous balls of Example 1 range in size from 100 to 5000 μm with penetrating pores formed therein. The pores were found to have a controlled hierarchical structure within a predetermined size range. In detail, pores hundreds nm in size were formed on pores one μm in size and interconnected with pores tens of nanometers in size. Over a pore size range, a uniform pore size distribution was detected.

EXAMPLE 2

Porous Ceramic Balls 2

The same procedure as in Example 1 was repeated, with the exception that (Poly-ethylene oxide)$_{100}$(Poly-propylene oxide)$_{65}$(Poly-ethylene oxide)$_{100}$ was used instead of the tri-block copolymer of step 1 of Example 1.

Figure 4:
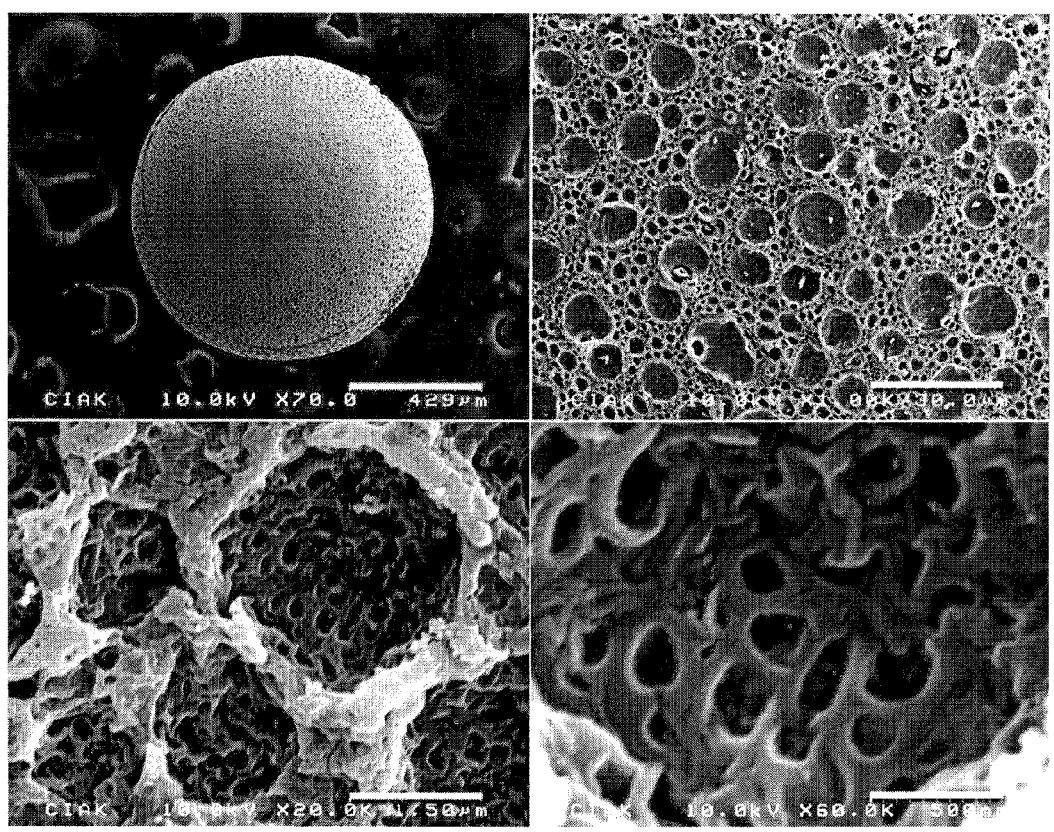
FIG. 4 is of scanning electron microphotographs of porous ceramic balls according to an embodiment of present invention.

Referring to FIG. 4, scanning electron microscope photographs of the porous ceramic balls are shown.

As seen in these SEM photographs, the porous ceramic balls of Example 2 were found to be similar in morphology to those of Example 2.

EXAMPLE 3

Preparation of Bioactive Porous Ceramic Balls

Figure 12:
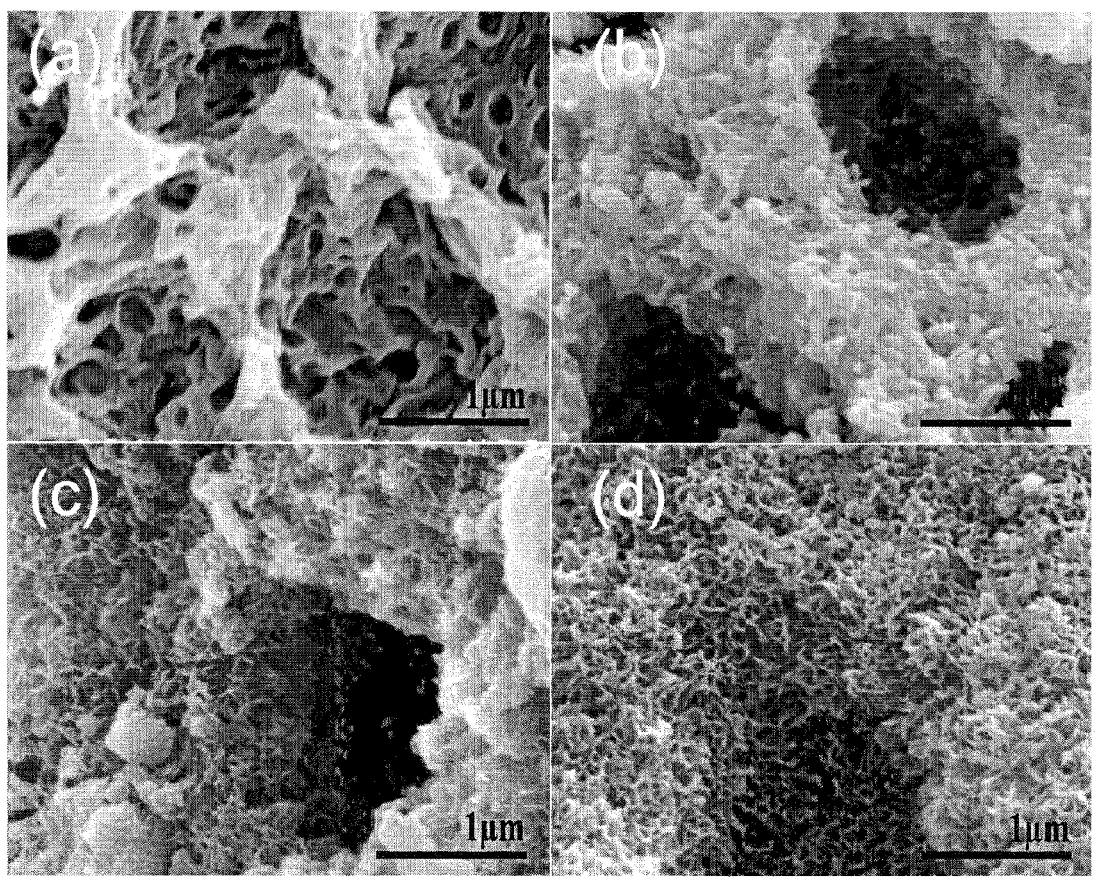
FIG. 12 is of SEM photographs showing the formation of apatite in porous ceramic balls according to an embodiment of the present invention (after 0 hour (a), 1 hour (b), 4 hours (c), and 24 hours (d))

The porous ceramic balls of Example 1 were immersed for 1, 4 and 24 hours in simulated body fluid to allow apatite crystals to grow therein. The SEM photographs of the porous ceramic balls with apatite crystals grown therein are given in FIG. 12.

As seen in these SEM photographs, apatite crystals are formed even after immersion for 1 hour in simulated body fluid, in comparison to no apatite crystals before immersion in the simulated body. Further, following lapses of 4 and 24 hours, apatite crystals in the simulated body fluid uniformly grow over the surfaces of the hierachically interconnected pores within the porous ceramic balls. In addition, the apatite crystals are in tens of nanometers of size, similar to the dimension of actual bones, with a needle-like morphology.

COMPARATIVE EXAMPLE 1

Preparation of Nanoparticles

The same procedure as in Example 1 was conducted, with the exception that (Poly-ethylene oxide)$_5$(Poly-propylene oxide)$_{68}$(Poly-ethylene oxide)$_5$ was used instead of the tri-block copolymer of step 1 of Example 1.

COMPARATIVE EXAMPLE 2

Preparation of Nanoparticles

The same procedure as in Example 1 was conducted, with the exception that (Poly-ethylene oxide)$_{20}$ (Poly-propylene oxide)$_{70}$(Poly-ethylene oxide)$_{20}$ was used instead of the tri-block copolymer of step 1 of Example 1.

EXPERIMENTAL EXAMPLE 1

Formation of Reverse Micelle According to Polymer characteristics

Figure 2:
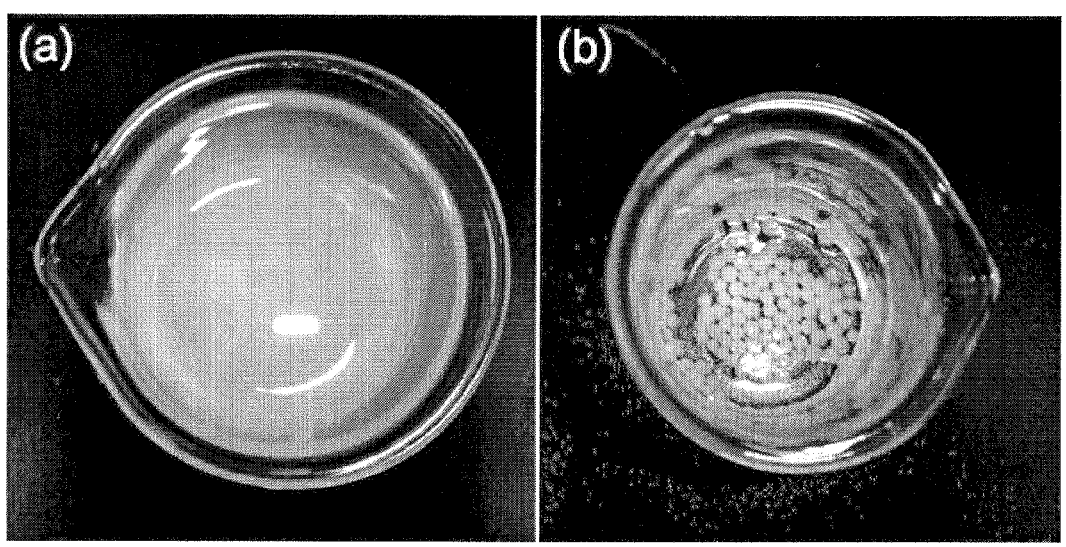
FIG. 2 shows photographs of experiments being carried out according to the present invention (Comparative Example 1 (a), Comparative Example 2 (b))

The tri-block copolymer, composed of hydrophilic moiety-hydrophobic moiety-hydrophilic moiety, serving as a polymer template, was examined for the formation of reverse micelles according to the ratio of hydrophilic moiety to hydrophobic moiety. For this, the porous ceramic balls of Examples 1 and 2 and Comparative Examples 1 and 2 were observed and photographed, as seen in FIG. 2.

When tri-block copolymers containing a long hydrophilic moiety were used as in Examples 1 and 2, transparent gel was formed just after dropping into the chloroform solvent. The spherical transparent gel reduced in size while starting to slowly turn opaque from the outer side. Even during this reduction in size, the gel was observed to keep a spherical shape (FIG. 2(*b*)). Drying and thermal treatment made these spherical gels semi-transparent or opaque.

In contrast, when tri-block copolymers containing a relatively short hydrophilic moiety were used as in Comparative Examples 1 and 2, spherical gels were formed just after being dropped into the chloroform solvent, but started to lose their morphologies with the lapse of time. After a certain time, the gel completely lost its shape and transformed into a sol state. A series of chloroform removal, drying and thermal treatment resulted in transparent ceramic powder (FIG. 2(*a*)).

EXPERIMENTAL EXAMPLE 2

Pore Distribution of Porous Ceramic Balls

The porous ceramic balls of Example 1 were evaluated for pore distribution using Hg-porosimetry (a) and a nitrogen adsorption method (b). The results are given in FIG. 5.

Figure 5:
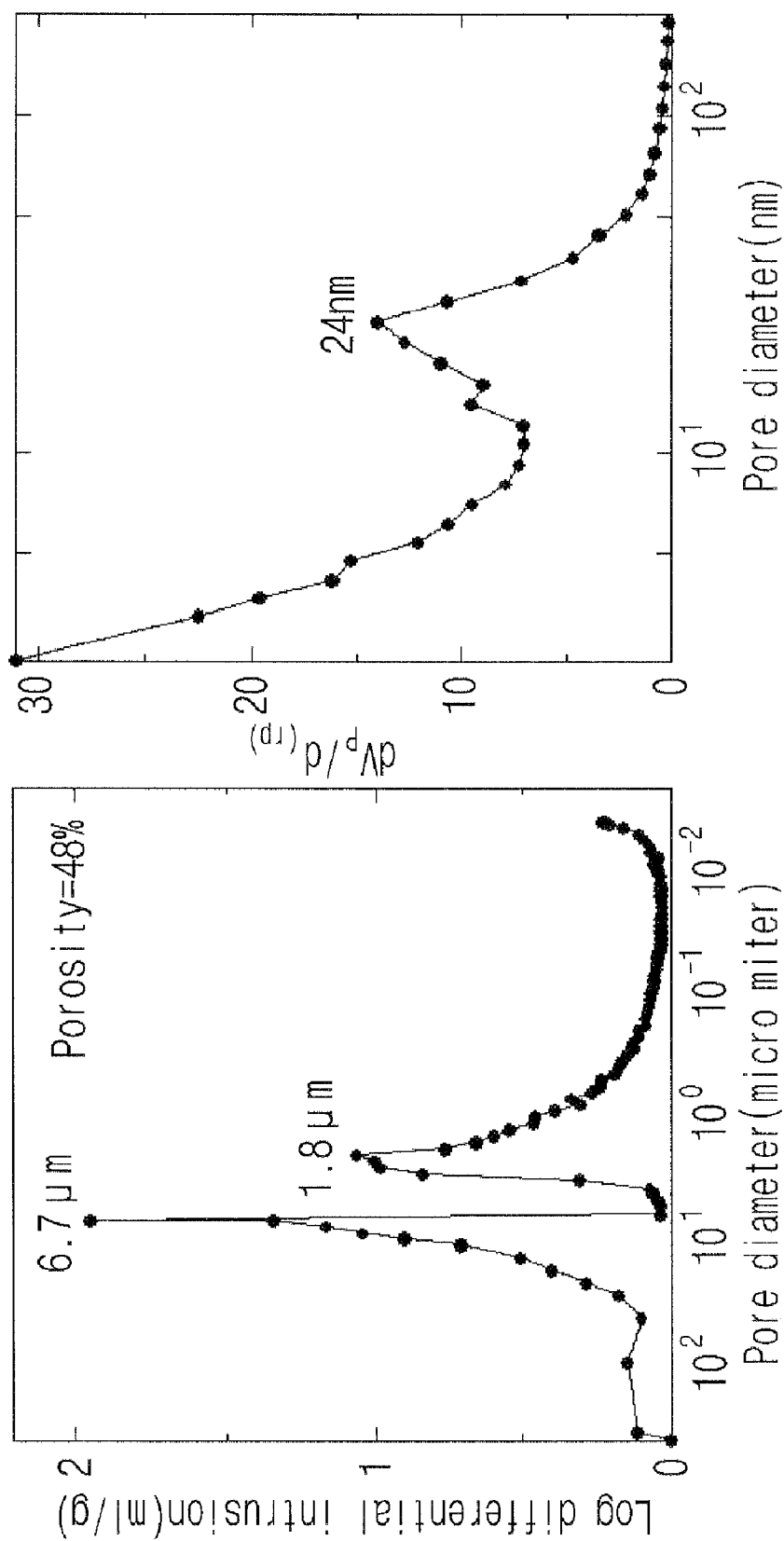
FIG. 5 is of pore distribution diagrams of porous ceramic balls according to an embodiment of the present invention (Hg-porosimetry (a), nitrogen adsorption (b))

As seen in FIG. 5, peaks are detected at sizes of 7 µm, 2 µm and 24 nm in the pore size distribution diagrams of the ceramic balls of Example 1, and a high porosity of about 50% is observed therein.

EXPERIMENTAL EXAMPLE 3

Specific Surface Area of Porous Ceramic Balls

Figure 6:
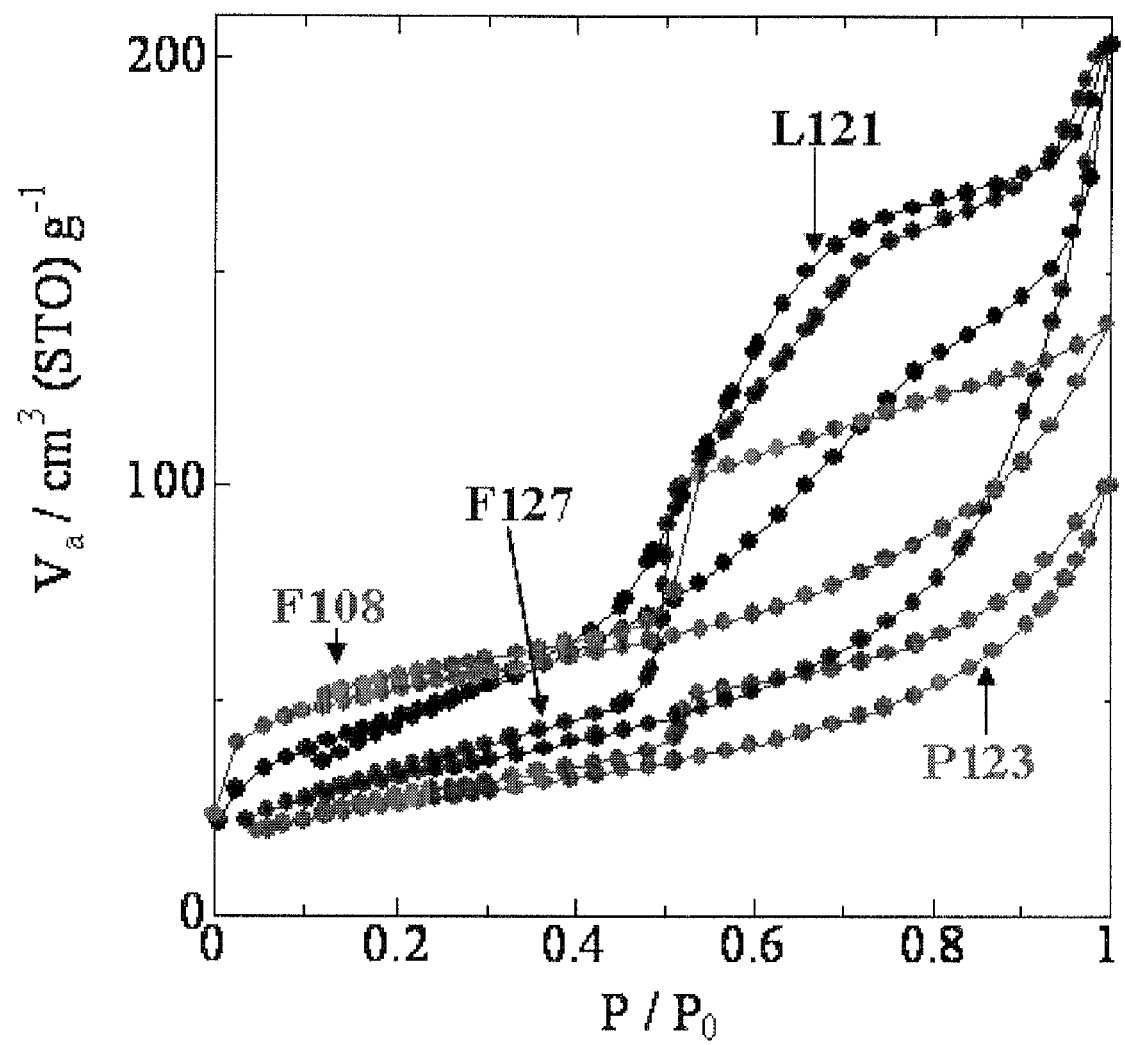
FIG. 6 is a hysteresis diagram of porous ceramic balls according to an embodiment of the present invention after nitrogen adsorption and desorption.

The porous ceramic balls of Examples 1 and 2 and Comparative Examples 1 and 2 were measured for specific surface area using a nitrogen adsorption method, and the results are given in Table 1 and FIG. 6.

TABLE 1

| Polymers | $M_{ave}$ | x/y | $S_{BET}/m^2 \cdot g^{-1}$ | Pore volume/cc · $g^{-1}$ |
|---|---|---|---|---|
| Example 1 | 14600 | 2.64 | 180 | 0.21 |
| Example 2 | 12600 | 1.54 | 117 | 0.3 |
| C. Example 1 | 5750 | 94 | 94 | 0.15 |
| C. Example 2 | 440 | 170 | 170 | 0.3 |

As shown in Table 1, the porous ceramic balls of Example 1 have a large specific surface area (185 m$^2$/g). The specific surface area of the porous ceramic balls of Example 2 was measured to be 117 m$^2$/g, which is smaller than that of Example 1, but larger than that of Comparative Example 1.

The specific surface area was 94 m$^2$/g for Comparative Example 1 which is smaller than that of Example 1 or 2. On the other hand, the particles of Comparative Example 2 had a specific surface area of 170 m$^2$/g which was similar to that of the porous ceramic balls of Example 1.

Further, as seen in the hysteresis curves of FIG. 6, all the pores formed on the porous ceramic balls of Examples 1 and 2 and Comparative Examples 1 and 2 are in nano-size ranges.

Figure 7:
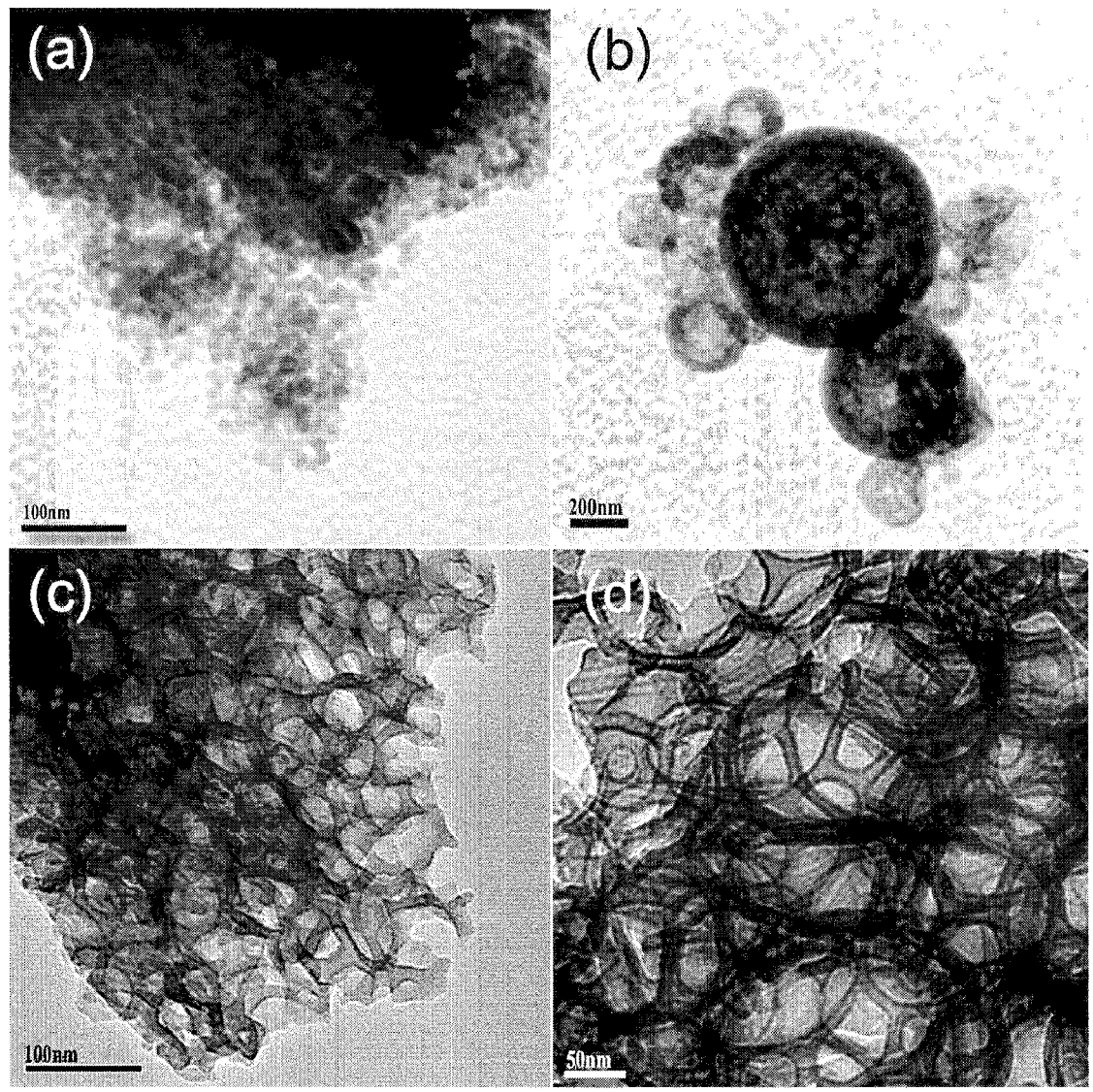
FIG. 7 is of transmission electron microphotographs of porous ceramic balls according to an embodiment of the present invention (Comparative Example 1 (a), Comparative Example 2 (b), Example 2 (c), Example 1 (d))

The nanoparticles of Comparative Example 2 showed a specific surface area as high as that of the porous ceramic balls of Example 1. Although they did not contain pores in nano-structures, the particles of Comparative Example 2 were as small as 10 nm in size so that their external surface area was extended to induce a large specific surface area. Also, since the hydrophilic moiety of the polymer template is longer in Comparative Example 2 than in Comparative Example 1, larger particles were formed than those formed in Comparative Example 1. It was observed that individual nanoparticles aggregated to form mega-particles (FIG. 7).

EXPERIMENTAL EXAMPLE 4

Pore Morphology According to Immersion Time Period

In order to examine the change of pore morphology with the time period of immersion, ceramic balls were prepared in the same manner as in Example 1, with the exception that they were immersed for 0.5, 2 and 24 hours. They were photographed using SEM in FIG. 9 and TEM in FIG. 10, and their specific surface area was measured as in FIG. 11.

Figure 9:
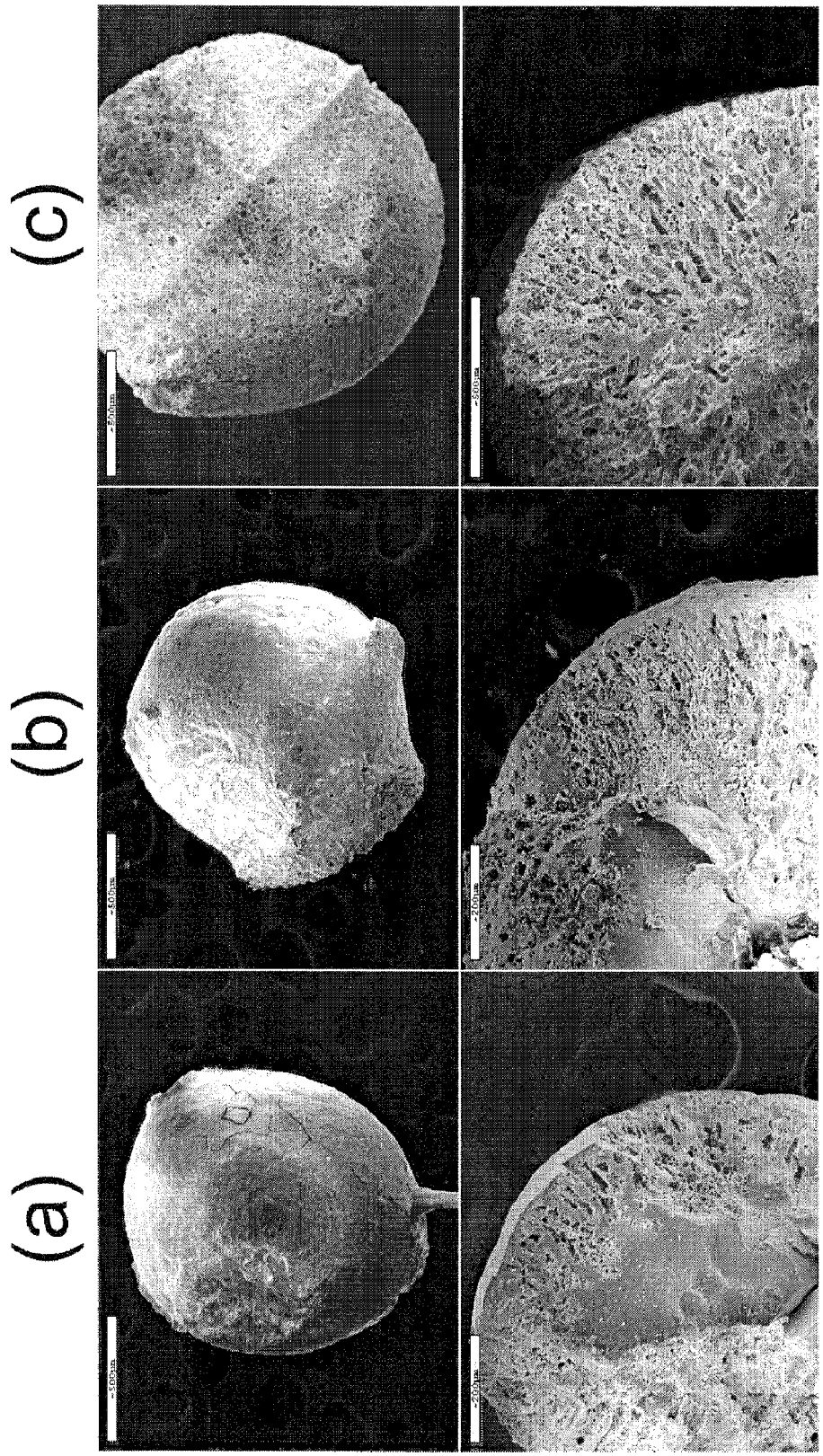
FIG. 9 is of SEM photographs showing changes in the morphology and cross sections of porous ceramic balls with immersion time in accordance with an embodiment of the present invention (upper panels; morphology change, lower panels; cross-section change, after 30 min (a); 2 hours (b); 24 hours (c))

As seen in FIG. 9, the ceramic balls (a) obtained after immersion for 30 min in chloroform were observed to have smooth surfaces with micropores formed partially thereon. Extended micropores were found on the surface of the ceramic ball (b) after immersion for 2 hours while nanopores are formed on the surface of the ceramic ball (c) after immersion for 24 hours.

Figure 10:
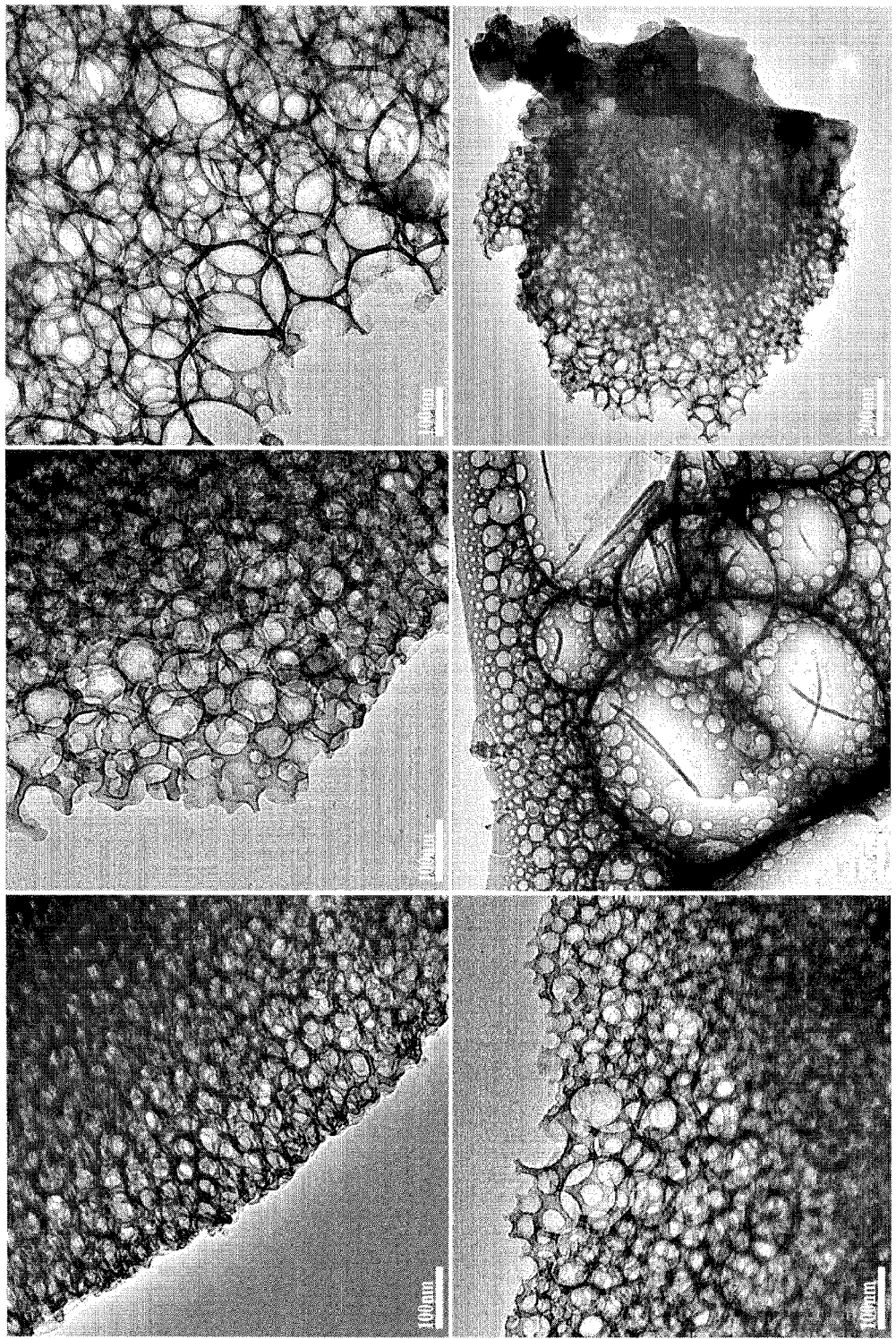
FIG. 10 is of TEM photographs showing changes in the morphology and cross sections of porous ceramic balls with immersion time in accordance with an embodiment of the present invention (upper panels; morphology change, lower panels; cross-section change, after 30 min (a); 2 hours (b); 24 hours (c))

As seen in FIG. 10, porous structures with a size of several nanometers which are constructed by the polymer micelles on the external surface which is in contact with chloroform are partially detected while pores with a size of tens of nanometers are formed therein. As the time period of immersion is increased, the pores tend to extend to the inwards of the balls and increase in size to tens of nanometers. After immersion for 24 hours, pores of micro-size had advanced to the innermost parts of the balls to produce a hierarchical porous structure in which pores of tens of nanometers are formed on the surface of pores of hundreds of nanometers.

Figure 11:
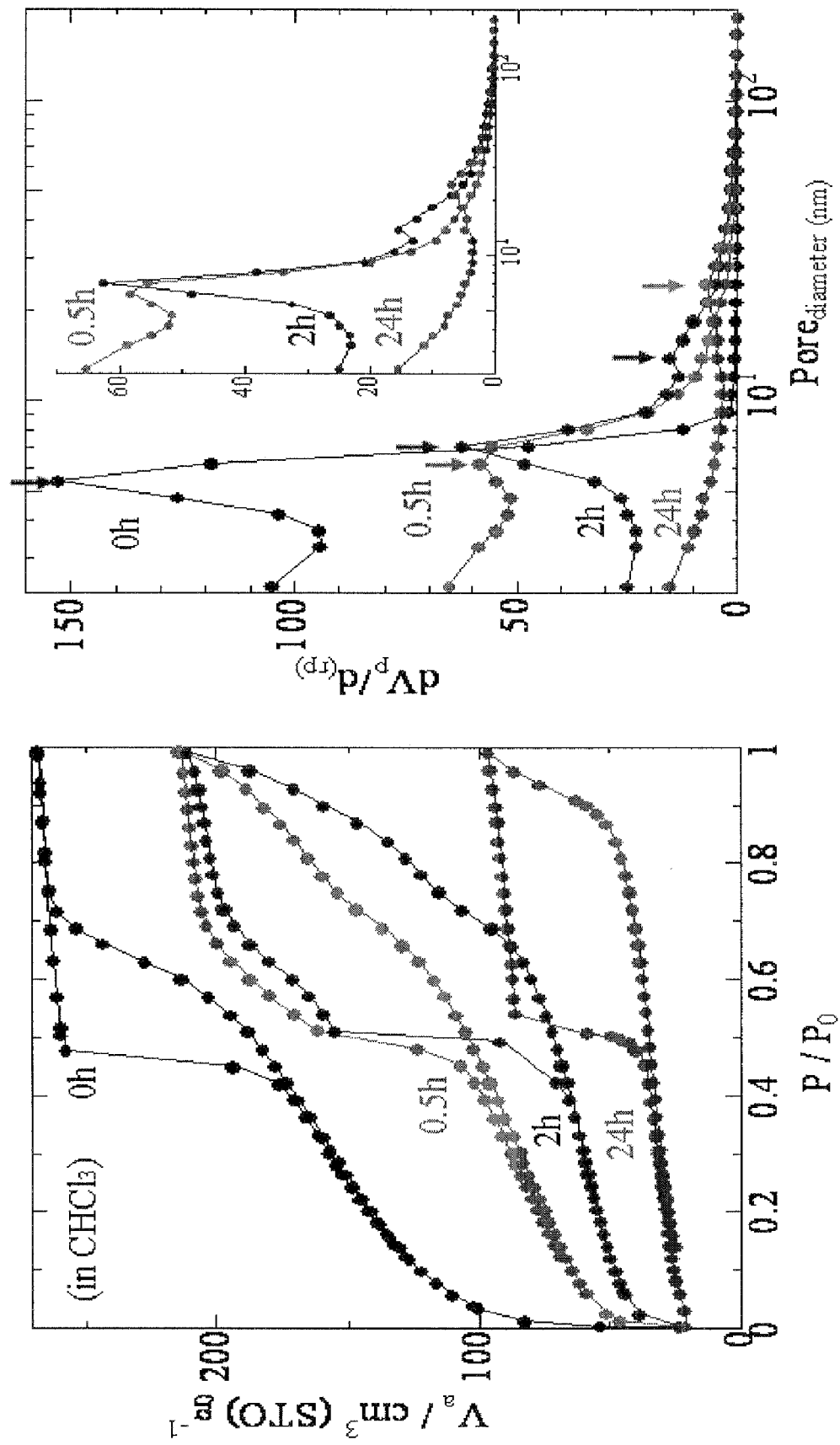
FIG. 11 is of graphs showing the change in porous structure with immersion time of porous ceramic balls according to an embodiment of the present invention (nitrogen adsorption/desorption contours (a), BJH plots (b))

As seen in FIG. 11, the three-dimensional porous structures with a size of nanometers formed in Example 1 was found to increase in pore size and decrease in specific surface area with the lapse of immersion time. As well, a change was detected in pore distribution with longer immersion times.

EXPERIMENTAL EXAMPLE 5

Assay for Bioactivity

Figure 13:
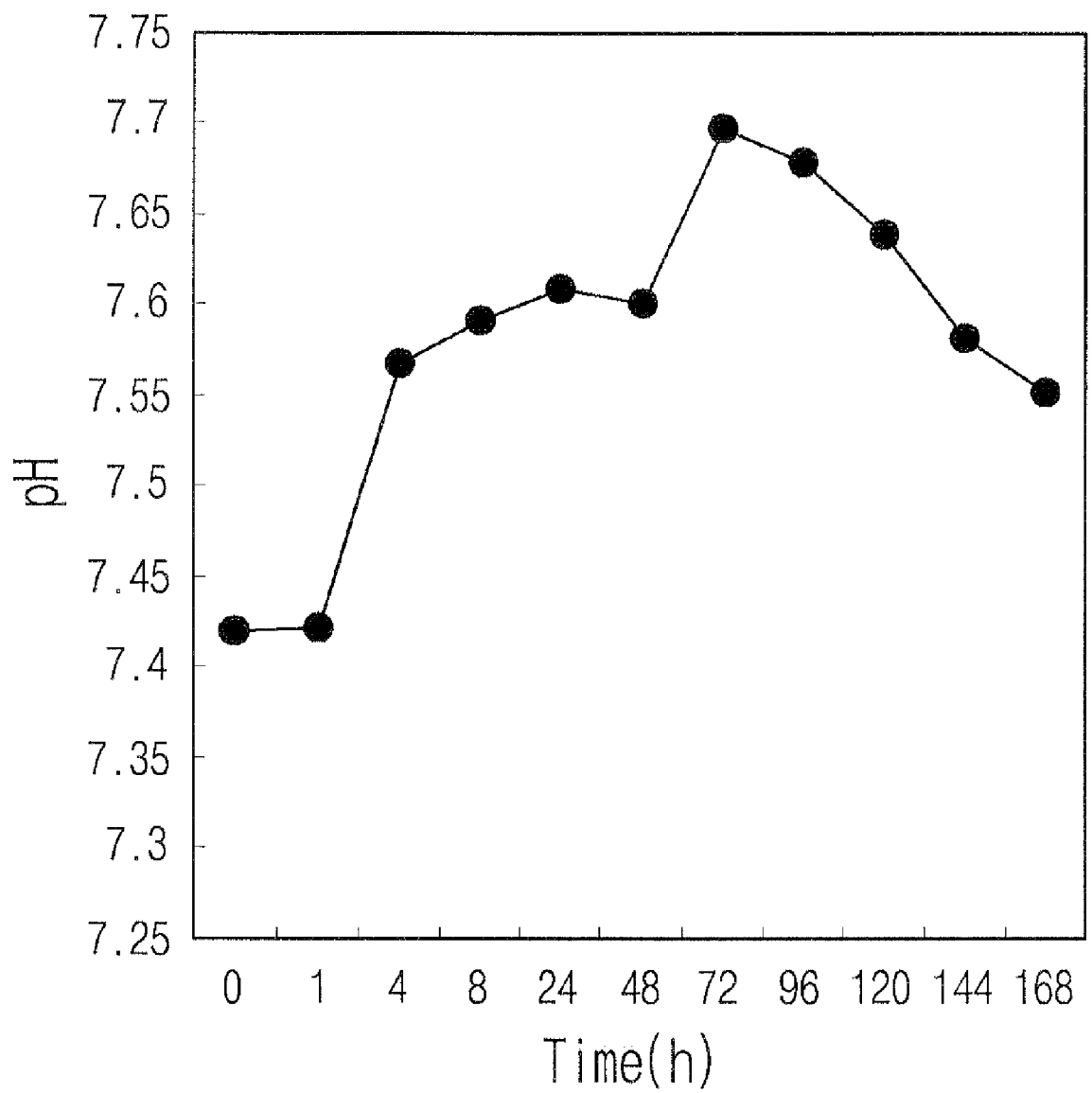
FIG. 13 is a graph showing the pH change of a solution containing porous ceramic balls according to an embodiment of the present invention.

In order to assay the ceramic balls of the present invention for applicability to biomaterials, especially bone fillers and bone scaffolds, the ceramic balls of Example 3 were examined for pH change in simulated body fluid with time, and the results are shown in FIG. 13.

As seen in FIG. 13, during the precipitation of porous bioactive glass in simulated body fluid, pH values were found to increase with the elution of Ca ions from the bioactive glass and decrease with the re-precipitation of Ca ions in a repetitive manner, indicating that the degradation of bioactive glass and the formation of apatite crystals occur sequentially or simultaneously.

Taken together, the data obtained in the examples demonstrate that the porous ceramic balls according to the present invention are bioactive to a sufficiently high degree as to induce osteogenesis and thus can be used as bone scaffolds useful in tissue engineering.

As described hitherto, the porous ceramic balls have a hierarchical porous structure ranging in size from nanometers to micrometers. Self-assembly polymers and sol-gel reactions are used to prepare porous ceramic balls in which pores ranging in size from ones of nanometers to tens of micrometers are hierarchically interconnected to one another. This hierarchical porous structure ensures high specific surface areas and porosities for the porous ceramic balls. Further, the size and distribution of the pores can be simply controlled with variations in hydrophobic solvent and reaction time.

The pore formation through polymer self-assembly and sol-gel reactions can be applied to ceramic and transition metals. Porous structures based on bioceramic materials, such as bioactive glass, allow the formation of apatite therein and thus can be used as biomaterials for bioengineering, including bone fillers, bone reconstruction materials, bone scaffolds, etc.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A porous ceramic ball, having a hierarchical porous structure in which pores with a size of 10~100 µm are constructed, with pores having a size of 0.1~10 µm formed on the surface thereof, and pores with a size of 1~100 nm are formed on the surface of the pores having a size of 0.1~10 µm, said pores being interconnected with one another.

2. The porous ceramic ball according to claim 1, ranging in size from 100 to 3,000 µm.

3. The porous ceramic ball according to claim 1, wherein the porous ceramic ball is a ceramic selected from a group consisting of silica, titania, alumina, calcium oxide and phosphorus oxide.

4. The porous ceramic ball according to claim 1, ranging in porosity from 40 to 80%.

5. A method for preparing a porous ceramic ball according to claim 1, comprising:
preparing a polymer template solution (step 1);
preparing a precursor solution (step 2);
mixing and reacting the polymer template of step 1 with the precursor of step 2 to give a mixed solution having an increased viscosity (step 3);
immersing the mixed solution of step 3 in a hydrophobic solvent to form reverse micelles and subjecting the reverse micelles to a sot-gel reaction to produce a ball (step 4); and
aging, drying, and thermally treating the ball of step 4 to remove the polymer template therefrom (step 5).

6. The method according to claim 5, wherein the polymer template is a tri-block copolymer composed of (hydrophilic moiety)$_x$(hydrophobic moiety)$_y$(hydrophilic moiety)$_x$.

7. The method according to claim 6, wherein the hydrophilic moiety is selected from a group consisting of poly alkyl (acrylic)acid, polyacrylamide, poly(N,N-dimethyl acrylamide), poly(N-isopropyl acrylamide), polyethylene glycol, polyethylene oxide, poly(methyl vinyl ether), poly(styrene sulfonic acid), polyvinyl alcohol), poly(2-vinyl N-methyl pyridinium iodide), poly(N-vinyl imidazole), poly(ethylene imine), and a mixture thereof.

8. The method according to claim 7, wherein the poly alkyl (acrylic) acid is selected from among poly(acrylic acid), poly (α-ethylacrylic acid), poly(α-propylacrylic acid), poly(methacrylic acid), poly(sodium acrylate), poly(sodium methacrylate) and poly(2-hydroxyethyl methacrylate); and the poly (ethylene imine) is selected from among poly(N-vinylamine), poly(N-vinyl formamide), poly(N-vinyl isobutyramide) and poly(N-vinyl pyrrolidone).

9. The method according to claim 6, wherein the hydrophobic moiety is selected from a group consisting of polyolefin, polybutadiene, polyisoprene, poly(N-vinyl imidazole), polylactone (lactide), polyisobutyl, polyoxirane, polyvinylpyridine, polysiloxane, polystyrene, poly(acrylonitrile), poly(adipic anhydride), poly(ethylene terephthalate), poly (ferrocenyldimethylsilane), poly(N-vinyl caprolactam), poly (N-vinyl carbazole), poly(sulfone ether), poly(vinyl acetate), polycarbonate, polyconidine, poly vinyl naphthalene, poly vinyl anthracene, and a mixture thereof.

10. The method according to claim 9, wherein the polyolefin has a backbone chain containing 1~20 carbon atoms; the polyalkyl(acrylate) is selected from among poly(benzyl α-ethyl acrylate), poly(benzyl α-propyl acrylate), poly(cyclohexyl methacrylate), poly(ethyl acrylate), poly(isopropyl acrylate), poly(ethyl methacrylate), poly(ethyl α-ethyl acrylate), poly(ethyl α-propyl acrylate), poly(fluorescein O-methacrylate)), poly(glycidyl methacrylate), poly(hydroxy propyl acrylate)), poly(isobornyl methacrylate), poly (iso-butyl methacrylate), poly(isocyanato ethyl methacrylate), poly(lautyl methacrylate), poly(methyl acrylate), poly (methylα-bromacrylate), poly(methyl methacrylate)-atactic, poly(N,N-dimethylaminoethyl methacrylate), poly(n-butyl acrylate), poly(n-butyl methacrylate), poly(neopentyl methacrylate), poly(n-hexyl methacrylate), poly(n-nonyl acrylate), poly(n-nonyl methacrylate), poly(n-octyl acrylate), poly(n-propyl methacrylate), poly(octadecyl methacrylate), poly(s-butyl methacrylate), poly(t-butyl acrylate), poly(t-butyl methacrylate), poly(t-butyl α-bromo-acrylate), poly(t-butyl α-ethylacrylate), poly(t-butyl α-propylacrylate), poly(tetrahydrofurfanyl methacrylate), poly(2,4-dimethyl-2,4-pentadienoate), poly(2-ethyl hexyl acrylate), poly(2-hydroxypropyl methacrylate), and poly(9-Anthracenyl methyl methacrylate;
the polyoxirane is selected from among poly(propylene oxide), poly(propylene glycol) dimethyl ether and poly (2,6-dimethyl-p-phenylene oxide);

the polysiloxane is selected from among poly(dimethyl siloxane), poly(ethyl methyl siloxane), poly(phenyl methyl siloxane) and poly(diethyl siloxane); and the polystyrene is selected from among poly($\alpha$-methyl styrene), poly(4-acetoxy styrene), poly (bromo styrene), poly chloro styrene), poly(4-dimethylsilyl styrene), poly(4-hydroxyl styrene), poly(4-methoxy styrene), poly(4-methyl styrene), poly(4-t-butyl styrene), poly (vinyl benzyl chloride) and poly(vinyl benzoic acid).

11. The method according to claim 6, wherein x is an integer of 1~150 and y is an integer of 1~100.

12. The method according to claim 11, wherein the ratio of x:y ranges from 0.5:1 to 1000:1.

13. The method according to claim 11, wherein the ratio of x:y ranges from 0.7:1 to 500:1.

14. The method according to claim 5, wherein the viscosity of step 3 is adjusted by drying the solvent.

15. The method according to claim 5, wherein the viscosity of step 3 ranges from 2000 cps to 35000 cps.

16. The method according to claim 5, wherein the immersing of step 4 is carried out by loading the mixed solution of step 3 in a syringe equipped with an extruder and dropwise adding the mixed solution to the hydrophobic solvent.

17. The method according to claim 5, wherein the ball of step 4 has a size and a morphology both of which are determined by the solution viscosity of step 3, a syringe needle size, or a dropping distance between the syringe and the hydrophobic solvent.

18. The method according to claim 5, wherein the hydrophobic solvent of step 4 is selected from among chloroform, carbon tetrachloride, benzene, o-dichlorobenzene, toluene, xylene, pentane, mesitylene, cyclohexane, hexane, heptane, diethyl ether, tetrachloroethylene acetonitrile, dimethyl sulfoxide, dimethylformamide, trichloroethylene and a mixture thereof.

19. The method according to claim 5, wherein the thermal treatment of step 5 is carried out at a temperature of 400~800° C. for 3~5 hours.

20. A bioactive bone scaffold based on the porous ceramic bail of claim 1.

* * * * *